United States Patent
Wainer et al.

(10) Patent No.: US 9,650,352 B2
(45) Date of Patent: May 16, 2017

(54) USE OF (2R, 6R)-HYDROXYNORKETAMINE, (S)-DEHYDRONORKETAMINE AND OTHER STEREOISOMERIC DEHYDRO AND HYDROXYLATED METABOLITES OF (R,S)-KETAMINE IN THE TREATMENT OF DEPRESSION AND NEUROPATHIC PAIN

(71) Applicants: The United States of America, as Represented by the Secretary, Department of Health and Human Service, Washington, DC (US); Cooper Health System, Camden, NJ (US); SRI International, Menlo Park, CA (US)

(72) Inventors: Irving W. Wainer, Washington, DC (US); Ruin Moaddel, Bel Air, MD (US); Michel Bernier, Pikesville, MD (US); Carlos A. Zarate, Germantown, MD (US); Marc C. Torjman, Southampton, PA (US); Michael E. Goldberg, Philadelphia, PA (US); Mary J. Tanga, Los Altos, CA (US)

(73) Assignees: THE UNITED STATES OF AMERICA, AS REPRESENTED BY THE SECRETARY, DEPARTMENT OF HEALTH AND HUMAN SERVICES, Washington, DC (US); COOPER HEALTH SYSTEM, Camden, NJ (US); SRI INTERNATIONAL, Menlo Park, CA (US)

(*) Notice: Subject to any disclaimer, the term of this patent is extended or adjusted under 35 U.S.C. 154(b) by 144 days.

(21) Appl. No.: 14/351,441

(22) PCT Filed: Oct. 15, 2012

(86) PCT No.: PCT/US2012/060256
§ 371 (c)(1),
(2) Date: Apr. 11, 2014

(87) PCT Pub. No.: WO2013/056229
PCT Pub. Date: Apr. 18, 2013

(65) Prior Publication Data
US 2014/0296241 A1 Oct. 2, 2014

Related U.S. Application Data

(60) Provisional application No. 61/547,336, filed on Oct. 14, 2011.

(51) Int. Cl.
C07D 295/155 (2006.01)
C07C 225/20 (2006.01)
C07C 237/04 (2006.01)
C07D 295/108 (2006.01)
C07D 295/112 (2006.01)
C07C 229/48 (2006.01)
C07C 237/20 (2006.01)
C07D 295/15 (2006.01)

(52) U.S. Cl.
CPC ........ *C07D 295/155* (2013.01); *C07C 225/20* (2013.01); *C07C 229/48* (2013.01); *C07C 237/04* (2013.01); *C07C 237/20* (2013.01); *C07D 295/108* (2013.01); *C07D 295/112* (2013.01); *C07D 295/15* (2013.01); *C07B 2200/07* (2013.01); *C07C 2101/14* (2013.01); *C07C 2101/16* (2013.01)

(58) Field of Classification Search
None
See application file for complete search history.

(56) References Cited

U.S. PATENT DOCUMENTS

| 8,785,500 B2 | 7/2014 | Charney et al. |
| 2009/0197297 A1 | 8/2009 | Murray et al. |

FOREIGN PATENT DOCUMENTS

| EP | 0623343 A1 | 11/1994 |
| WO | 9707750 A1 | 3/1997 |
| WO | 2004045601 | * 6/2004 |

(Continued)

OTHER PUBLICATIONS

Adams et al., Biomedical Mass Spectrometry (1981), 8(11), 527-38.*

(Continued)

*Primary Examiner* — Karl J Puttlitz
(74) *Attorney, Agent, or Firm* — Cantor Colburn LLP

(57) ABSTRACT

The disclosure provides pharmaceutical preparations containing (2R,6R)-hydroxynorketamine, or (R)- or (S)-dehydronorketamine, or other stereoisomeric dehydro or hydroxylated ketamine metabolite. (2R,6R)-hydroxynorketamine The disclosure also provides novel ketamine metabolite prodrugs. The disclosure provides methods of treating, bipolar depression, major depressive disorder, neuropathic and chronic pain, including complex regional pain disorder (CRPS) by administering a purified ketamine metabolite or a ketamine metabolite prodrug directly to patients in need of such treatment.

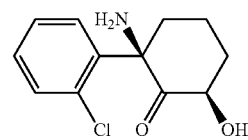

22 Claims, No Drawings

(56) References Cited

FOREIGN PATENT DOCUMENTS

| WO | 2004045601 A1 | 6/2004 |
|---|---|---|
| WO | 2009131794 A1 | 10/2009 |

OTHER PUBLICATIONS

Database CAPLUS Chemical Abstracts Service, Columbus, Ohio, US; Database Accession No. 1976:25675, Abstract of Needham et al., Journal of Chromatography (1975), 114(1), 220-2.*

Database CAPLUS Chemical Abstracts Service, Columbus, Ohio, US; Database Accession No. 1987:590266, Abstract of Woolf et al., Xenobiotica (1987), 17(7), 839-47.*

Leung et al., J. Med. Chem. 1986,29, 2396-2399.*

Adams et al., "Studies on the Biotransformation of Ketamine 1-Identification of Metabolites Producedin Vitro from Rat Liver Microsomal Preparations" Biological Mass Spectrometry; vol. 8, No. 11, Nov. 1, 1981, pp. 527-538.

Baumgart et al., "D-Amino Acids in the Brain: the Biochemistry of Brain Serine Racemase" FEBS Journal 275 (2008), 3538-3545.

Jiraskova-Vanickova et al., Inhibition of Human Serine Racemase, an Emerging Target for Medicinal Chemistry: Current Drug Targets, 12, (2011), pp. 1037-1055.

Leung et al., "Comparative Pharmacology in the Rat of Ketamine and its Two Prinvipal Metabolites, Norketamine and (Z)-6-hydroxynorketamine" Journal of Medicinal Chemistry, American Chemical Society; vol. 29, No. 11, Jan. 1, 1986, pp. 2396-2399.

Moaddel et al., "(R,S)-Dehydronorketamine and (2S,6S)-Hydroxynorketamine are Nicotinic Acetylcholine Receptor Inhibitors: Reexamining the "Ketamine Paradigm" in Complex Regional Pain Syndrome (CRPS)" Presented at ASA, (2011), 1 Page.

International Search Report of the International Searching Authority for International Patent Application No. PCT/US2012/060256; International Filing Date: Oct. 15, 2012; Date of mailing: Jan. 30, 2013; 7 Pages.

Written Opinion of the International Searching Authority for International Patent Application No. PCT/US2012/060256; International Filing Date: Oct. 15, 2012; Date of mailing: Jan. 30, 2013; 11 Pages.

Shimoyama et al., "Oral Ketamine is Antinociceptive in the Rat Formalin Test: Role of the Metabolite, Norketamine" Pain, vol. 81, No. 1-2, May 1, 1999, pp. 85-93.

Singh et al., "Capillary Electrophoresis-Laser Induced Fluorescence (CE-LIF) Assay for Measurement of Intra-Cellular D-Serine and Serine Racemase Activity" Elsevier Editorial System(tm) for Analytical Biochemistry Manuscript Draft, Manuscript No. ABIO-11-849, Aug. 9, 2011.

Wolosker et al- "D-Amino Aids in the Brain: D-serine in Neurotransmission and Neurodegeneration" FEBS Journal 275 (2008) 3514-3526.

Woolf et al., "Synthesis of (Z)- and (E)-6-hydroxyketamine" The Journal of Organic Chemistry; vol. 49, No. 18, Sep. 1, 1984, pp. 3305-3310.

Yoshimura et al., "Amino Acids in the Brain: Structure and Function of Pyridoxal Phosphate-dependent Amino Acid Racemases" FEBS Journal 275 (2008) 3527-3537.

Desta et al.; "Stereoselective and regiospecific hydroxylation of ketamine and norketamine"; Xenobiotica, vol. 42, No. 11; 2012; pp. 1076-1087.

Zhao et al.; "Simultaneous population pharmacokinetic modelling of ketamine and three major metabolites in patients with treatment-resistent bipolar depression"; Br. J. Clin. Pharmacol., vol. 72, No. 2; 2012; pp. 304-314.

Goldbeg et al., "Pharmacodynamic Profiles of Ketamine (R)- and (S)- with 5-Day Inpatient Infusion for the Treatment of Complex Regional Pain Syndrome" Pain Physician 2010: 13: 378-387.

Zarate et al.; "Relationship of Ketamine's Plasma Metabolites with Response, Diagnosis, and Side Effects in Major Depression"; Biol. Psych., vol. 72; 2012; pp. 331-338.

Krystal, I. H., "N-methyl-D-aspartate Glutamate Receptor Antagonists and the Promise of Rapid-Acting Antidepressants" Archives of General Psychiatry 2010, vol. 67, Issue 11, pp. 1110-1111.

Mager, D. E., et al., "Simultaneous population pharmacokinetic modelling of ketamine and three major metabolites in patients with treatment-resistant bipolar depression" British Journal of Clinical Pharmacology 2012, vol. 72, Issue 4, pp. 304-314.

Moaddel, R., et al., "A parallel chiral-achiral liquid chromatographic method for the determination of the stereoisiomers of ketamine and ketamine metabolites in the plasma and urine of patients with complex regional pain syndrome" Talanta, 2010, vol. 82, pp. 1892-1904.

Moaddel, R., et al., "Sub-anesthetic concentrations of (R,S)-ketamine metabolites inhibit acetylcholine-evoked currents in (alpha) 7 nicotinic acetylcholine receptors" European Journal of Pharmacology, 2013, vol. 698, pp. 228-234.

Moaddel, R., et al., "The distribution and clerance of (2S,6S)-hydroxynorketamine, an active ketamine metabolite, in Wistar rats" Pharmacology Research & Perspectives, 2015, vol. 3[4], 10 pages.

Paul, R. K., et al., "(R,S)-Ketamine Metabolites (R,S)-norketamine and (2S,6S)-hydroxynorketamine increase the Mammalian Target of Rapamycin Function" Anesthesiology, 2014, 121, pp. 149-159.

Singh, N. S., et al., "What is hydroxynorketamine and what can it bring to neurotherapeutics?" Expt Rev Neurotherapeutics, 2014, 14(11), pp. 1239-1242.

Van Velzen, M. & Dahan, A., "Ketamine Metabolomics in the Treatment of Major Depression" Anesthesiology (2014), vol. 121, 4-5.

Vranken, I. H., et al., "Neuropathological findings after continuous intrathecal administration of S(+)-ketamine for the management of neuropathic cancer pain" Pain 2005, vol. 117, pp. 231-235.

Zarate, C., et al., "Glutamatergic Modulators: The Future of Treating Mood Disorders?" Haravard Review of Psychiatry, 2010, vol. 18, No. 5, pp. 293-303.

* cited by examiner

USE OF (2R, 6R)-HYDROXYNORKETAMINE, (S)-DEHYDRONORKETAMINE AND OTHER STEREOISOMERIC DEHYDRO AND HYDROXYLATED METABOLITES OF (R,S)-KETAMINE IN THE TREATMENT OF DEPRESSION AND NEUROPATHIC PAIN

CROSS-REFERENCE TO RELATED APPLICATIONS

This application is a National Stage of International Patent Application No. PCT/US2012/060256, filed Oct. 15, 2012, which claims priority from U.S. Provisional Application No. 61/547,336, filed Oct. 14, 2011, both of which are hereby incorporated by reference in their entirety.

STATEMENT OF GOVERNMENT SUPPORT

The Intramural Research Program of the National Institute of Aging and the Nation Institute of Mental Health funded the subject matter of this disclosure. The United States Government has certain rights in this application.

BACKGROUND

Ketamine, a drug currently used in human anesthesia and veterinary medicine, has been shown in clinical studies to be effective in the treatment of several conditions, including the of treatment-resistant bipolar depression, major depressive disorder, neuropathic pain, and chronic pain, including complex regional pain syndrome (CRPS).

In the current "ketamine paradigm", ketamine and norketamine (NK) are considered to be responsible for the antinociceptive response in CRPS patients. However the routine use of the drug is hindered by unwanted central nervous system (CNS) effects. Approximately 30% of patients do not respond to ketamine treatment. Additionally, ketamine treatment is associated with serious side effects due to the drug's anesthetic properties and abuse potential.

Recent studies have demonstrated that in CRPS patients receiving a continuous 5-day infusion of (R,S)-ketamine the primary circulating metabolites were (R,S)-dehydronorketamine (DHNK) and (2S,6S;2R,6R)-hydroxynorketamine (HNK). The data suggest that downstream metabolites play a role in ketamine analgesic efficacy, although little is known about the metabolites' pharmacological activity.

The need for therapeutics which exhibits the therapeutic properties of ketamine with efficacy in a higher percentage of patients, reduced anesthetic properties and reduced abuse liability exists. The present disclosure fulfills this need and provides additional advantages set forth herein.

FIELD OF THE DISCLOSURE

This disclosure demonstrates that an active agents responsible for the therapeutic response to ketamine in patients is primarily due to (2R,6R)-hydroxynorketamine and (S)-dehydronorketamine, ketamine metabolite. The disclosure provides pharmaceutical preparations containing ketamine metabolites and prodrug of ketamine metabolites. The disclosure also provides novel ketamine prodrugs. The disclosure provides methods of treating, bipolar depression, neuropathic and chronic pain, including complex regional pain synthetic pain syndrome (CRPS) by administering purified (2R,6R)-hydroxynorketamine or purified (S)-dehydronorketamine or a prodrug of these compounds directly to patients in need of such treatment.

SUMMARY

In a first aspect the disclosure provides a pharmaceutical composition comprising a compound of Formula I

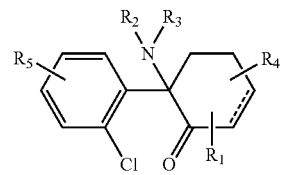

Formula I or a pharmaceutically acceptable salt thereof, together with a pharmaceutically acceptable excipient. Within Formula I the variables, e.g. $R_1$-$R_4$, carry the definitions set forth below.

$R_1$ is hydrogen, hydroxyl, or a group -$A_1B_1$ where $A_1$ is —O—, —O(C=O)—, —(C=O)O—, —O(C=O)O, —O(C=O)$NR_6$—, —OS(O)$_2$—, —OS(O)$_3$, or —OP(O)$_3$—, and $B_1$ is $C_1$-$C_8$alkyl, $C_2$-$C_8$alkenyl, $C_2$-$C_8$alkynyl, (carbocycle)$C_0$-$C_4$alkyl, (heterocycle)$C_0$-$C_4$alkyl, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy.

The six-membered ring to which $R_1$ is bound contains a double bond when $R_1$ is hydrogen and is fully saturated when $R_1$ is hydroxyl or -$A_1B_1$;

$R_2$ is hydrogen or -$A_2B_2$ where $A_2$ is a bond, —O(C=O)—, —(C=O)O—, —S(O)$_2$—, —(S=O)$NR_6$—, or —(C=O)$NR_6$—, $B_2$ is $C_1$-$C_8$alkyl, $C_2$-$C_8$alkenyl, $C_2$-$C_8$alkynyl, $C_2$-$C_6$alkanoyl, (carbocycle)$C_0$-$C_4$alkyl, (heterocycle)$C_0$-$C_4$alkyl, or an amino acid or dipeptide covalently bound to $A_2$ by its C-terminus, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy.

$R_3$ is hydrogen or $C_1$-$C_6$alkyl.

$R_4$ and $R_5$ are 0 or 1 or more substituents independently chosen from halogen, hydroxyl, amino, cyano, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy.

$R_6$ is hydrogen or $C_1$-$C_6$alkyl.

Also included are prodrugs of ketamine metabolites, including prodrugs of all hydroxynorketamine diastereomers, including (2R,6R)-hydroxynorketamine, (R) and (S)-dehydronorketamine, and other stereoisomeric dehydro and hydroxylated ketamine metabolites. These prodrugs carry the definition set forth above for compounds of Formula I however the following conditions may apply:

$R_1$ is not hydrogen or hydroxyl when $R_2$ is hydrogen.
$B_1$ is methyl when $A_1$ is —O—.
$A_1B_1$ is not (4-methylphenyl)-S(O)$_2$O—.
$B_1$ is not methyl when $A_1$ is a bond.
$B_2$ is not methyl when $A_2$ is a bond or —(C=O)O—.

In another aspect the disclosure provides a method of treating bipolar depression, major depressive disorder, schizophrenia, Alzheimer's dementia, amyotrophic lateral sclerosis, complex regional pain syndrome (CRPS), chronic pain, or neuropathic pain comprising administering a pharmaceutical composition containing an effective amount of a compound of Formula I or a pharmaceutically acceptable salt thereof, together with a pharmaceutically acceptable carrier to a patient in need of such treatment.

The disclosure also includes a method of treating bipolar depression, schizophrenia, Alzheimer's dementia, amyotrophic lateral sclerosis, complex regional pain syndrome (CRPS), chronic pain, or neuropathic pain comprising administering an effective amount of isolated hydroxynorketamine diastereomers, such as (2R,6R)-hydroxynorketamine or isolated (R)- or (S)-dehydronorketamine to a patient in need of such treatment.

In yet another aspect the disclosure includes a method of treating a patient for bipolar depression, complex regional pain syndrome (CRPS), chronic pain, or neuropathic pain comprising (1) determining that the patient is a ketamine non-responder; and (2) administering an effective amount of isolated hydroxynorketamine diastereomer, such as (2R,6R)-hydroxynorketamine or isolated (R)- or (S)-dehydronorketamine to the patient.

Applicants have determined that certain compounds of Formula I are potent serine racemase inhibitors. The disclosure also provides a method of inhibiting serine racemase comprising contacting cells with a concentration of a compound of Formula I sufficient to inhibit serine racemase in vitro.

DETAILED DESCRIPTION

Terminology

Compounds disclosed herein are described using standard nomenclature. Unless defined otherwise, all technical and scientific terms used herein have the same meaning as is commonly understood by one of skill in the art to which this disclosure belongs.

The terms "a" and "an" do not denote a limitation of quantity, but rather denote the presence of at least one of the referenced item.

Formula I includes all subformulae thereof. For example Formula I includes compounds of Formulas I and subformulae Formula II-V and the pharmaceutically acceptable salts, prodrugs and other derivatives, hydrates, polymorphs, and thereof.

The term "chiral" refers to molecules, which have the property of non-superimposability of the mirror image partner.

"Stereoisomers" are compounds, which have identical chemical constitution, but differ with regard to the arrangement of the atoms or groups in space.

A "Diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Where a compound exists in various tautomeric forms, the invention is not limited to any one of the specific tautomers, but rather includes all tautomeric forms.

The disclosure includes compounds of Formula I having all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $R_1$-$R_4$. Unless otherwise specified, each variable within Formula I is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds.

The term "substituted", as used herein, means that at least one hydrogen on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —$(CH_2)C_3$-$C_7$cycloalkyl is attached through carbon of the methylene ($CH_2$) group.

"Alkyl" includes both branched and straight chain saturated aliphatic hydrocarbon groups, having the specified number of carbon atoms, generally from 1 to about 12 carbon atoms. The term $C_1$-$C_6$alkyl as used herein indicates an alkyl group having from 1 to about 6 carbon atoms. When $C_0$-$C_n$ alkyl is used herein in conjunction with another group, for example, (phenyl)$C_0$-$C_4$ alkyl, the indicated group, in this case phenyl, is either directly bound by a single covalent bond ($C_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkanoyl" is an alkyl group as defined above, attached through a keto (—(C=O)—) bridge. Alkanoyl groups have the indicated number of carbon atoms, with the carbon of the keto group being included in the numbered carbon atoms. For example a $C_2$alkanoyl group is an acetyl group having the formula $CH_3(C=O)$—.

"Alkenyl" means straight and branched hydrocarbon chains comprising one or more unsaturated carbon-carbon bonds, which may occur in any stable point along the chain. Alkenyl groups described herein typically have from 2 to about 12 carbons atoms. Preferred alkenyl groups are lower alkenyl groups, those alkenyl groups having from 2 to about 8 carbon atoms, e.g. $C_2$-$C_8$, $C_2$-$C_6$, and $C_2$-$C_4$ alkenyl groups. Examples of alkenyl groups include ethenyl, propenyl, and butenyl groups.

"Alkoxy" means an alkyl group, as defined above, with the indicated number of carbon atoms attached via an oxygen bridge. Examples of alkoxy include, but are not limited to, methoxy, ethoxy, 3-hexoxy, and 3-methylpentoxy.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

"Alkylester" indicates an alkyl group as defined above attached through an ester linkage. The ester linkage may be in either orientation, e.g. a group of the formula —O(C=O) alkyl or a group of the formula —(C=O)Oalkyl.

A "carbocycle" is a 3 to 8 membered saturated, partially unsaturated, or aromatic ring containing only carbon ring atoms or a 6 to 11 membered saturated, partially unsaturated, or aromatic bicyclic carbocylic ring system containing only carbon ring atoms. Unless otherwise indicated, the carbocycle may be attached to its pendant group it substitutes at any carbon atom that results in a stable structure. When indicated the carbocyclic rings described herein may be substituted on any available ring carbon if the resulting compound is stable. Carbocyclic groups include, cycloalkyl groups, such as cyclopropyl and cyclohexyl; cycloalkenyl groups, such as cyclohexenyl, bridged cycloalkyl groups; and aryl groups, such as phenyl.

"Cycloalkyl" indicates saturated hydrocarbon ring groups, having the specified number of carbon atoms, usually from 3 to about 7 ring carbon atoms. Examples of cycloalkyl groups include cyclopropyl, cyclobutyl, cyclopentyl, or cyclohexyl.

The term "heterocycle" indicates a 5- to 8-membered saturated, partially unsaturated, or aromatic ring containing from 1 to about 4 heteroatoms chosen from N, O, and S, with remaining ring atoms being carbon, or a 7 to 11 membered bicyclic saturated, partially unsaturated, or aromatic heterocyclic ring system or a 10 to 15-membered tricyclic ring system, containing at least 1 heteroatom in the multiple ring system chosen from N, O, and S and containing up to about 4 heteroatoms independently chosen from N, O, and S in each ring of the multiple ring system. Unless otherwise indicated, the heterocyclic ring may be attached to the group it substitutes at any heteroatom or carbon atom that results in a stable structure. When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

"5- or 6-membered heteroaryl" indicates a stable 5- to 6-membered monocyclic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Heterocycloalkyl" means a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

"Haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge (oxygen of an alcohol radical).

"Halo" or "halogen" as used herein refers to fluoro, chloro, bromo, or iodo.

An "active agent" means any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms.

"Administration" means dispensing a compound or composition containing the compound for use via any appropriate route, for example, oral administration, in either solid or liquid dosage form, inhalation, injection, suppository administration, or transdermal contact. "Administration" also include applying a compound or composition containing the compound via any appropriate route such as via oral administration, in either solid or liquid dosage form, inhalation, injection, suppository administration, or transdermal contact. "Administration" does not include in vivo formation of the compound by a metabolic pathway in a person or animal who has consumed or been treated with ketamine or norketamine.

"Depressive symptoms" include low mood, diminished interest in activities, psychomotor slowing or agitation, changes in appetite, poor concentration or indecisiveness, excessive guilt or feelings of worthlessness, and suicidal ideations may occur in the context of depressive disorders, bipolar disorders, mood disorders due to a general medical condition, substance-induced mood disorders, other unspecified mood disorders, and also may be present in association with a range of other psychiatric disorders, including but not limited to psychotic disorders, cognitive disorders, eating disorders, anxiety disorders and personality disorders. The longitudinal course of the disorder, the history, and type of symptoms, and etiologic factors help distinguish the various forms of mood disorders from each other.

"Depression symptoms rating scale" refers to any one of a number of standardized questionnaires, clinical instruments, or symptom inventories utilized to measure symptoms and symptom severity in depression. Such rating scales are often used in clinical studies to define treatment outcomes, based on changes from the study's entry point(s) to endpoint(s). Such depression symptoms rating scales include, but are not limited to, The Quick Inventory of Depressive-Symptomatology Self-Report (QIDS-SR$_{16}$), the 17-Item Hamilton Rating Scale of Depression (HRSD$_{17}$), the 30-Item Inventory of Depressive Symptomatology (IDS-C$_{30}$), or The Montgomery-Asperg Depression Rating Scale (MADRS). Such ratings scales may involve patient self-report or be clinician rated. A 50% or greater reduction in a depression ratings scale score over the course of a clinical trial (starting point to endpoint) is typically considered a favorable response for most depression symptoms rating scales. "Remission" in clinical studies of depression often refers to achieving at, or below, a particular numerical rating score on a depression symptoms rating scale (for instance, less than or equal to 7 on the HRSD$_{17}$; or less than or equal to 5 on the QIDS-SR$_{16}$; or less than or equal to 10 on the MADRS).

A "patient" means any human or non-human animal in need of medical treatment. Medical treatment can include treatment of an existing condition, such as a disease or disorder, prophylactic or preventative treatment, or diagnostic treatment. In some embodiments the patient is a human patient.

"Pharmaceutical compositions" are compositions comprising at least one active agent, such as a compound or salt of Formula I, and at least one other substance, such as a carrier, excipient, or diluent.

The term "carrier" applied to pharmaceutical compositions of the invention refers to a diluent, excipient, or vehicle with which an active compound is administered.

A "pharmaceutically acceptable excipient" means an excipient that is useful in preparing a pharmaceutical composition that is generally safe, non-toxic, and neither biologically nor otherwise undesirable, and includes an excipient that is acceptable for veterinary use as well as human pharmaceutical use. A "pharmaceutically acceptable excipient" as used in the present application includes both one and more than one such excipient.

"Pharmaceutically acceptable salts" are derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH$_2$)$_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like, and combinations comprising one or more of the foregoing salts.

"Prodrug" means any compound that becomes compound of the invention when administered to a mammalian subject, e.g., upon metabolic processing of the prodrug. Examples of prodrugs include, but are not limited to, acetate, formate, and benzoate and like derivatives of functional groups (such as alcohol or amine groups) in the compounds of the invention.

The term "therapeutically effective amount" or "effective amount" means an amount effective, when administered to a human or non-human patient, to provide any therapeutic benefit. A therapeutic benefit may be an amelioration of symptoms, e.g., an amount effective to decrease the symptoms of a depressive disorder or pain. A therapeutically effective amount of a compound is also an amount sufficient to provide a significant positive effect on any indicia of a disease, disorder, or condition e.g. an amount sufficient to significantly reduce the frequency and severity of depressive symptoms or pain. A significant effect on an indicia of a disorder or condition includes a statistically significant in a standard parametric test of statistical significance such as Student's T-test, where p<0.05; though the effect need not be significant in some embodiments.

Chemical Description

Compound Structure

The following structure is given by Leung and Baillie (*J. Med. Chem.*, (1986) 29: 2396-2399)

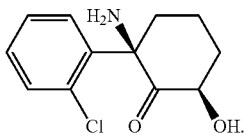 [SMILES: N[C@@]1(c2ccccc2Cl)CCC[C@@H](O)C1=O]

This compound is known as (Z)-6-hydroxynorketamine. The structure of (S)-dehydronorketamine is

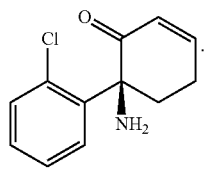

Its IUPAC name is (S)-1-amino-2'-chloro-5,6-dihydro-[1,1'-biphenyl]-2(1H)-one. Other compounds of this disclosure include:
(2S,6S)-hydroxynorketamine

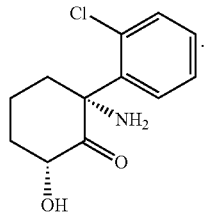 [SMILES: N[C@@]1(c2ccccc2Cl)CCC[C@@H](O)C1=O]

The disclosure includes all stereoisomers of hydroxynorketamine and dehydronorketamine.

The disclosure includes novel compounds that are prodrugs of hydroxynorketamine diastereomers, such as (2R,6R)-hydroxynorketamine, and (R)- and (S)-dehydronorketamine as well as prodrugs of stereoisomers of these compounds.

Compound Function

Without wishing to be bound to any particular theory applicants believe certain compounds of Formula I exert activity via serine racemase inhibition. Since nicotinic acetylcholine receptors (nAChR) have been validated as a target in analgesia applicants investigated the activity of DHNK at two nAChR subtypes, $\alpha_7$ and $\alpha_3\beta_4$ nAChR. Patch-clamp technique in a whole-cell configuration was used to examine functional activity of ketamine, norketamine, DHNK and FINK metabolites at the $\alpha 7$ and $\alpha 3\beta 4$ neuronal acetylcholinesterase receptors (nAChRs). The activity of these compounds at the $\alpha 3\beta 4$ nAChR was investigated using nicotine-stimulated 86Rb+ efflux assays in HEK293 cells expressing the $\alpha 3\beta 4$ nAChR. DHNK was identified as a potent inhibitor of the $\alpha_7$ nAChR ($IC_{50}$=0.05 µM) while were determined to be inactive ketamine and norketamine are inactive. DHNK is inactive at the $\alpha_3\beta_4$ nAChR while ketamine is a weak non-competitive inhibitor ($IC_{50}$=10 µM).

Applicants have determined that ketamine inhibits NMDA (N-methyl-D-aspartic acid) receptors by inhibiting serine racemase and thereby limiting the concentration of D-serine available to interact with the NMDA receptor. An indirect inhibition of SR activity by ketamine or ketamine metabolites through the inhibition of nAChR activity was hypothesized. PC12 cells were chosen to test the hypothesis since the cell line expresses active SR and $\alpha_7$ and $\alpha_3\beta_4$ nAChRs. Applicants determined DHNK is a potent and selective inhibitor of $\alpha 7$ nAChR that greatly reduces intracellular concentration of D-serine in 1321N1 astrocytoma cells (IC50=16.37 nM).

Contrary to the current "ketamine paradigm", it appears that downstream ketamine metabolites are active and can contribute to the clinically observed antinociceptive effects of the parent drug. This is consistent with the results of previous pharmacokinetic/pharmacodynamic studies indicating that ketamine and NK exposure alone do not explain ketamine's analgesic properties. In addition, ketamine's remarkable clinical efficacy in some CRPS patients may reflect individual differences in the ability to metabolize ketamine.

Compound Embodiments

In addition to pharmaceutical compositions containing compounds of Formula I, as defined in the "SUMMARY" section the disclosure include prodrugs of hydroxynorketamine diastereomers, such as (2R,6R)-hydroxynorketamine in which the variables, e.g., $R_1$-$R_6$ carry the following definitions. The disclosure includes compounds of Formula I having any combination of variable definitions that results in a stable compound.

Thus the disclosure includes compounds and salts of Formula I

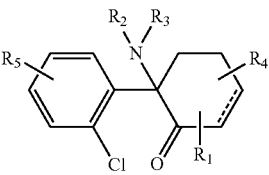

Formula I in which the following conditions are met.

Subformulae of Formula I

The disclosure includes compounds and salts of the following subformulae of Formula I.

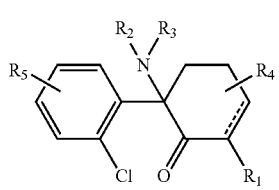

Formula II

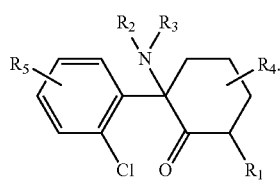

Formula III

In Formula III, R$_1$ is not H

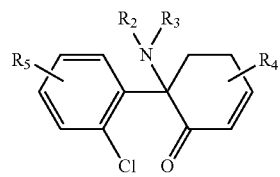

Formula IV

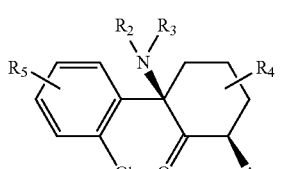

Formula V

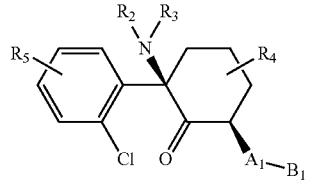

Formula VI

The disclosure also includes compounds and salts of Formula I-VI in which the 2-Chlorophenyl is replaced by a 2-fluorophenyl or 2-bromophenyl, each of which is substituted with R$_5$.

The disclosure also includes compounds of the formula

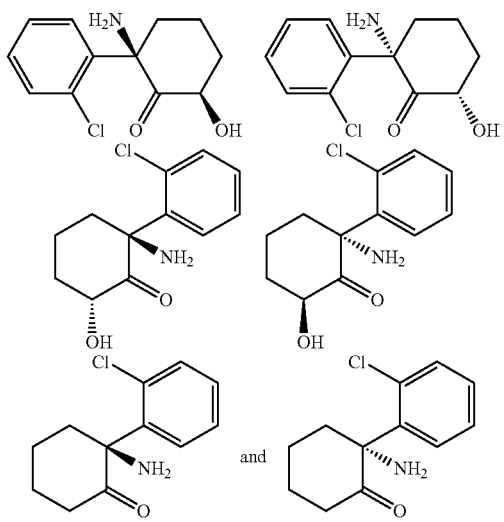

and the pharmaceutically acceptable salts thereof and pharmaceutical compositions containing these compounds and salts together with at least one pharmaceutically acceptable carrier.

In a particular embodiment the disclosure includes compounds of the formula

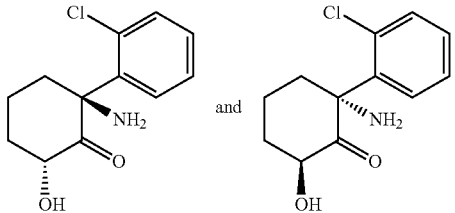 [SMILES: N[C@]1(c2ccccc2Cl)CCC[C@@H](O)C1=O ; N[C@@]1(c2ccccc2Cl)CCC[C@H](O)C1=O]

and the pharmaceutically acceptable salts thereof and pharmaceutical compositions containing one or both of these compounds or salts thereof and at least one pharmaceutically acceptable carrier.

Prodrug Compounds

Also included are prodrug compounds and salts of Formula I, in which the variables R$_1$-R$_4$ carry the following definitions.

R$_1$ is hydrogen, hydroxyl or -A$_1$B$_1$ where A$_1$ is —O—, —O(C=O)—, —(C=O)O—, —O(C=O)O—, —O(C=O)NR$_6$—, —OS(O)$_2$—, —OS(O)$_3$, or —OP(O)$_3$—, and B$_1$ is C$_1$-C$_8$alkyl, C$_2$-C$_8$alkenyl, C$_2$-C$_8$alkynyl, (carbocycle)C$_0$-C$_4$alkyl or (heterocycle)C$_0$-C$_4$alkyl, each of which is substituted with from 0 to 4 substituents independently chosen from halogen, hydroxyl, amino, cyano, C$_1$-C$_4$alkyl, C$_1$-C$_4$alkoxy, C$_1$-C$_6$alkylester, mono- and di-(C$_1$-C$_4$alkyl)amino, (C$_3$-C$_7$cycloalkyl)C$_0$-C$_2$alkyl, (heterocycloalkyl)C$_0$-C$_2$alkyl, C$_1$-C$_2$haloalkyl, and C$_1$-C$_2$haloalkoxy; with the proviso that -A$_1$B$_1$ is not (4-methylphenyl)-S(O)$_2$O—.

The six-membered ring to which R$_1$ is bound is fully saturated when R$_1$ is hydroxyl or -A$_1$B$_1$.

R$_2$ is hydrogen or -A$_2$B$_2$ where A$_2$ is a bond, —O(C=O)—, —(C=O)O—, —S(O)$_2$—, —(S=O)NR$_6$—, or —(C=O)NR$_6$—, B$_2$ is C$_1$-C$_8$alkyl, C$_2$-C$_8$alkenyl, C$_2$-C$_8$alkynyl, C$_2$-C$_6$alkanoyl, (carbocycle)C$_0$-C$_4$alkyl, (heterocycle)C$_0$-C$_4$alkyl, or an amino acid or dipeptide covalently bound to A$_2$ by its C-terminus, each of which is substituted with from 0 to 4 substituents independently chosen from halogen, hydroxyl, amino, cyano, C$_1$-C$_4$alkyl, C$_1$-C$_4$alkoxy, C$_1$-C$_6$alkylester, mono- and di-(C$_1$-C$_4$alkyl)amino, (C$_3$-C$_7$cycloalkyl)C$_0$-C$_2$alkyl, (heterocycloalkyl)C$_0$-C$_2$alkyl, C$_1$-C$_2$haloalkyl, and C$_1$-C$_2$haloalkoxy; with the proviso that B$_2$ is not methyl when A$_2$ is a bond or —(C=O)O—.

R$_1$ is not hydrogen or hydroxyl when R$_2$ is hydrogen.

R$_3$ is hydrogen or C$_1$-C$_6$alkyl.

R$_4$ and R$_5$ are 0 or 1 or more substituents independently chosen from halogen, hydroxyl, amino, cyano, C$_1$-C$_4$alkyl, C$_1$-C$_4$alkoxy, mono- and di-C$_1$-C$_4$alkylamino, C$_1$-C$_2$haloalkyl, and C$_1$-C$_2$haloalkoxy.

R$_6$ is hydrogen or C$_1$-C$_6$alkyl.

Also included are embodiments in which the following conditions are met. These definitions can also be applied for methods of treatment and pharmaceutical compositions. The disclosure includes all combinations of these variables so long as a stable compound results.

(1) R$_1$ is hydrogen or hydroxyl.

R$_3$ is hydrogen or methyl.

R$_4$ and R$_5$ are each 0 to 2 substituents independently chosen from halogen, hydroxyl, amino, C$_1$-C$_2$alkyl, and C$_1$-C$_2$alkyl.

R$_6$ is hydrogen or methyl.

(2) R$_2$ is -A$_2$B$_2$ where A$_2$ is a bond, —(C=O)O—, —S(O)$_2$—, —(S=O)NR$_6$—, or —(C=O)NR$_6$—, B$_2$ is C$_1$-C$_6$alkyl, C$_2$-C$_4$alkanoyl, (phenyl)C$_0$-C$_2$alkyl, (C$_3$-

$C_7$cycloalkyl)$C_0$-$C_4$alkyl, (heterocycloalkyl)$C_0$-$C_2$alkyl, (5- or 6-membered heteroaryl)$C_0$-$C_2$alkyl, or an amino acid covalently bound to $A_2$ by its C-terminus, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl) amino, $C_1$-$C_2$haloalkyl, and $C_1$-$C_2$haloalkoxy.

(3) $A_2$ is a bond and $B_2$ is an amino acid covalently bound to $A_2$ by its C-terminus.

(4) $B_2$ is

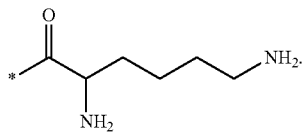

(5) $A_2$ is a bond or —(C=O)O— and $B_2$ is $C_2$-$C_6$alkyl, (phenyl)$C_0$-$C_2$alkyl, or ($C_3$-$C_7$alkyl)$C_0$-$C_4$alkyl, each of which is substituted with from 0 to 4 substituents independently chosen from halogen, hydroxyl, amino, cyano, $C_1$-$C_4$alkyl, $C_1$-$C_4$alkoxy, and mono- and di-($C_1$-$C_4$alkyl) amino.

(6) $R_2$ is hydrogen.
$R_3$ is hydrogen or methyl.
$R_4$ and $R_5$ are each 0 to 2 substituents independently chosen from halogen, hydroxyl, amino, $C_1$-$C_2$alkyl, and $C_1$-$C_2$alkyl.
$R_6$ is hydrogen or methyl.

(7) $R_1$ is -$A_1B_1$ where $A_1$ is —O(C=O)— or —O(C=O)O—, and $B_1$ is $C_1$-$C_6$alkyl, (phenyl)$C_0$-$C_4$alkyl, ($C_3$-$C_7$cycloalkyl)$C_0$-$C_4$alkyl, (heterocycloalkyl)$C_0$-$C_2$alkyl, or (5- or 6-membered heteroaryl)$C_0$-$C_2$alkyl, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl) amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy. In certain embodiments $R_1$ is -$A_1B_1$ and $A_1$ is —O— or $A_1$ is —O(C=O)—.

(8) $B_1$ is $C_1$-$C_6$alkyl, (phenyl)$C_0$-$C_2$alkyl, or (heterocycloalkyl)$C_0$-$C_2$alkyl, each of which is substituted with from 0 to 2 substituents independently chosen from halogen, hydroxyl, amino, cyano, $C_1$-$C_4$alkyl, $C_1$-$C_4$alkoxy, mono- and di-($C_1$-$C_4$alkyl)amino, ($C_3$-$C_7$cycloalkyl)$C_0$-$C_2$alkyl, and (heterocycloalkyl)$C_0$-$C_2$alkyl.

(9) A compound or salt of Formula IV in which
$R_3$ is hydrogen or methyl.
$R_4$ and $R_5$ are each 0 to 2 substituents independently chosen from halogen, hydroxyl, amino, $C_1$-$C_2$alkyl, and $C_1$-$C_2$alkyl.
$R_6$ is hydrogen or methyl.

Pharmaceutical Compositions

Compounds disclosed herein can be administered as the neat chemical, but are preferably administered as a pharmaceutical composition. Accordingly, the disclosure provides pharmaceutical compositions comprising a compound or pharmaceutically acceptable salt of Formula I, together with at least one pharmaceutically acceptable carrier. The pharmaceutical composition may contain a compound or salt of Formula I as the only active agent, but is preferably contains at least one additional active agent. In certain embodiments the pharmaceutical composition is an oral dosage form that contains from about 0.1 mg to about 1000 mg, from about 1 mg to about 500 mg, or from about 10 mg to about 200 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions can be formulated for oral administration. Preferred oral dosage forms are formulated for once a day or twice a day administration. These compositions contain between 0.1 and 99 weight % (wt. %) of a compound of Formula I and usually at least about 5 wt. % of a compound of Formula. Some embodiments contain from about 25 wt. % to about 50 wt. % or from about 5 wt. % to about 75 wt. % of the compound of Formula.

Methods of Treatment

Studies using sub-anesthetic does of (R,S)-Ketamine demonstrated that this drug is effective in the treatment of neuropathic and chronic pain, including the treatment of patients suffering from complex regional pain syndrome (CRPS). The analysis of the plasma samples obtained from CRPS patients receiving (R,S)-ketamine as a 5-day continuous infusion revealed that the primary drug, (R,S)-ketamine, was not primarily responsible for the therapeutic response This disclosure demonstrates that the active agents responsible for the therapeutic response to ketamine in patients are (2R,6R; 2S,6S)-hydroxynorketamine and (R,S)-dehydronorketamine, which are ketamine metabolites. These metabolites are produced by a number of liver enzymes identified as Cytochrome P450s (CYPs) including CYP2A6, CYP2B6, CYP2C9, CYP2D6, and CYP3A5. The CYPs are polymorphic, which means that they are not equally active in all humans. Thus it is likely that ketamine's failure to elicit a therapeutic response in about 30% of treated patients is due the activity differences of one or more of the identified CYPs among patients leading to unequal production of (2R,6R, 2S,6S)-hydroxynorketamine and/or (S)-dehydronorketamine.

The essence of the discovery is the identification of a new compound that can be administered directly to the patient in order to increase the response rate and to avoid treatment-limiting CNS side effects produced by (R,S)-ketamine. The CNS effects are associated with (R,S)-ketamine's activity at the NMDA receptor. (2R,6R; 2S,6S)-hydroxynorketamine (HNK) is not active at the NMDA receptor and thus avoids these side effects. Direct administration of the (2S,6S)-hydroxynorketamine metabolite and/or DHNK has the advantage of producing a therapeutic response in a greater percentage of patients than ketamine. (2S,6S)-hydroxynorketamine and DHNK also have a long plasma half-lives and are orally bioavailable. Thus, oral formulations for daily administration are included in the disclosure.

Methods of treatment include administering any one of (2S,6S)-hydroxynorketamine, (2R,6R)-hydroxynorketamine, (2S,6R)-hydroxynorketamine, (2R,6S)-hydroxynorketamine, (S)-dehydronorketamine, and (R)-dehydronorketamine, or any combination of the foregoing. Methods of treatment also include administering any of any one of (2S,6S)-hydroxynorketamine, (2R,6R)-hydroxynorketamine, (2S,6R)-hydroxynorketamine, (2R,6S)-hydroxynorketamine, (S)-dehydronorketamine, and (R)-dehydronorketamine in optically pure form.

The disclosure includes a methods of treating bipolar depression, major depressive disorder, schizophrenia, Alzheimer's dementia, amyotrophic lateral sclerosis, complex regional pain syndrome (CRPS), chronic pain, or neuropathic pain comprising administering a pharmaceutical composition containing an effective amount of a compound of Formula I or a pharmaceutically acceptable salt thereof, together with a pharmaceutically acceptable carrier to a patient in need of such treatment.

Methods of treatment include providing certain dosage amounts of a compound or pharmaceutically acceptable salt of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single unit dosage form will vary depending upon the patient treated and the particular mode of administration.

In certain embodiments a therapeutically effect amount is an amount that provide a plasma Cmax of a compound of Formula I of about of 0.25 mcg/mL to about 125 mcg/mL, or about 1 mcg/mL to about 50 mcg/mL. For peripheral indications formulations and methods that provide a Cmax of about 0.25 mcg/mL to about 25 mcg/mL are preferred, while for CNS indications, formulations and methods that provide a plasma Cmax of about 0.25 mcg/mL to about 125 mcg/mL are preferred. The disclosure also includes IV pharmaceutical compositions that provide about 0.2 mg to about 500 mg per dose of a compound of Formula I, for peripheral indications compounds that provide about 0.5 mg to about 500 mg/dose are preferred.

The compound or salt of Formula I may be the only active agent administered or may be administered together with an additional active agent. For example the compound of Formula I may administered together with another active agent that is chosen from any of the following:

Antidepressants: escitalopram, fluoxetine, paroxetine, duloxetine, sertraline, citalopram, bupropion, venlafaxine, duloxetine, naltrexone, mirtazapine, venlafaxine, atomoxetine, bupropion, doxepin, amitriptyline, clomipramine, nortriptyline, buspirone, aripiprazole, clozapine, loxapine, olanzapine, quetiapine, risperidone, ziprasidone, carbamazepine, gabapentin, lamotrigine, phenyloin, pregabalin, donepezil, galantamine, memantine, rivastigmine, tramiprosate, or pharmaceutically active salts or prodrugs thereof, or a combination of the foregoing;

Schizophrenia Medications: aripiprazole, lurasidone, asenapine, clozapine, ziprasidone, risperidone, quetiapine, stelazine, olanzapine, loxapine, flupentioxol, perphenazine, haloperidol, chlorpromazine, fluphenazine, prolixin, paliperidone;

Alzheimer's Dementia Medications: donepezil, rivastigmine, galantamine, memantine ALS Medications: riluzole Pain Medications: acetaminophen, aspirin, NSAIDS, including Diclofenac, Diflunisal, Etodolac, Fenoprofen, Flurbiprofen, Ibuprofen, Indomethacin, Ketoprofen, Ketorolac, Meclofenamate, Mefenamic Acid, Meloxicam, Nabumetone, Naproxen, Oxaprozin, Phenylbutazone, Piroxicam, Sulindac, Tolmetinopiods, Cox-2 inhibitors such as celcoxib, and narcotic pain medications such as Buprenorphine, Butorphanol, Codeine, Hydrocodone, Hydromorphone, Levorphanol, Meperidine, Methadone, Morphine, Nalbuphine, Oxycodone, Oxymorphone, Pentazocine, Propoxyphene, the central analgesic tramadol.

The preceding list of additional active agents is meant to be exemplary rather than fully inclusive. Additional active agents not included in the above list may be administered in combination with a compound of Formula I. The additional active agent will be dosed according to its approved prescribing information, though in some embodiments the additional active agent will be dosed at less the typically prescribed dose and in some instances less than the minimum approved dose.

The disclosure includes a method of treating bipolar depression and major depressive disorder where an effective amount of the compound is an amount effective to decrease depressive symptoms, wherein a decrease in depressive symptoms is the achievement of a 50% or greater reduction of symptoms identified on a depression symptom rating scale, or a score less than or equal to 7 on the $HRSD_{17}$, or less than or equal to 5 on the $QID-SR_{16}$, or less than or equal to 10 on the MADRS.

The disclosure provides an amount effective to decrease painful symptoms; wherein a decrease in painful symptom is the achievement of a 50% or greater reduction of painful symptoms on a pain rating scale.

EXAMPLES
Example 1
Synthesis of Lysine Conjugates of Norketamine
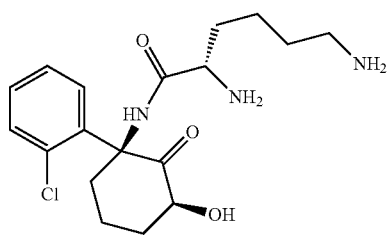
(2S,6S)-6-Hydroxynorketamine, N-lysine Derivative
Methodology:
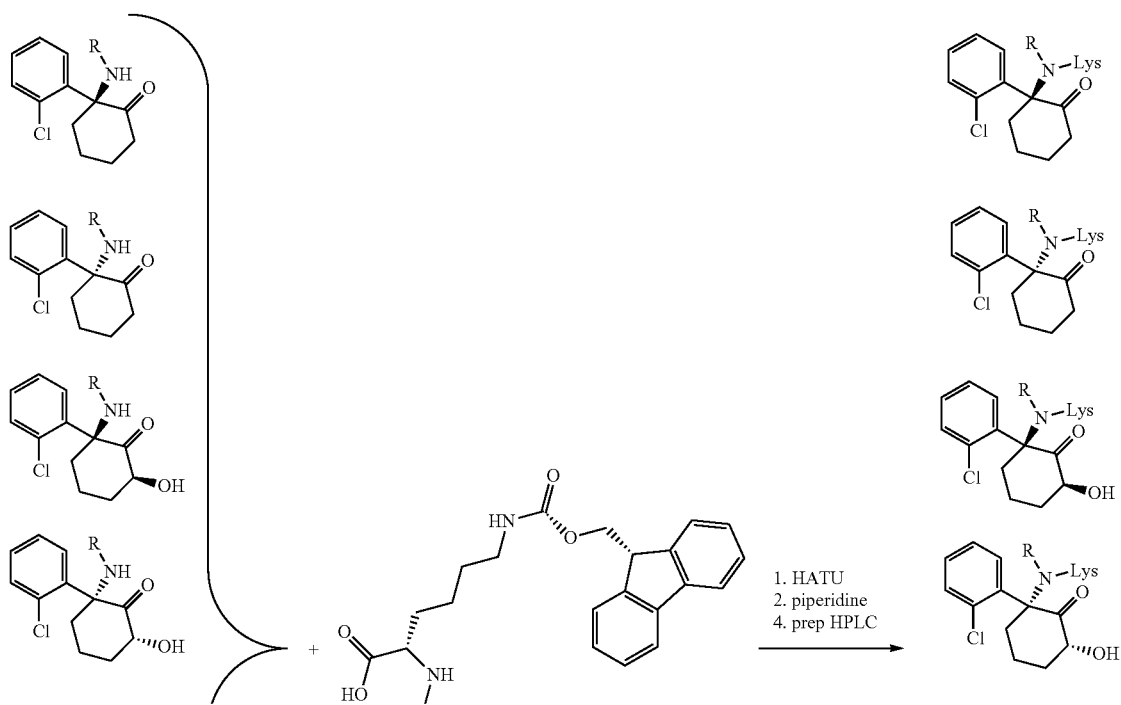

-continued
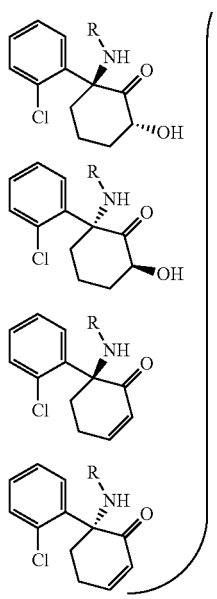 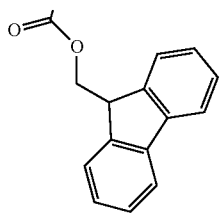 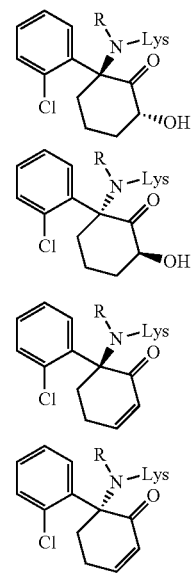
R = H, CH₃
Example 2
Synthesis of Ester Conjugates of 6-Hydroxynorketamine
Synthesis of Ester Conjugates of 6-Hydroxyketamines
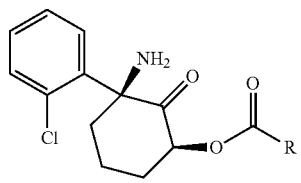

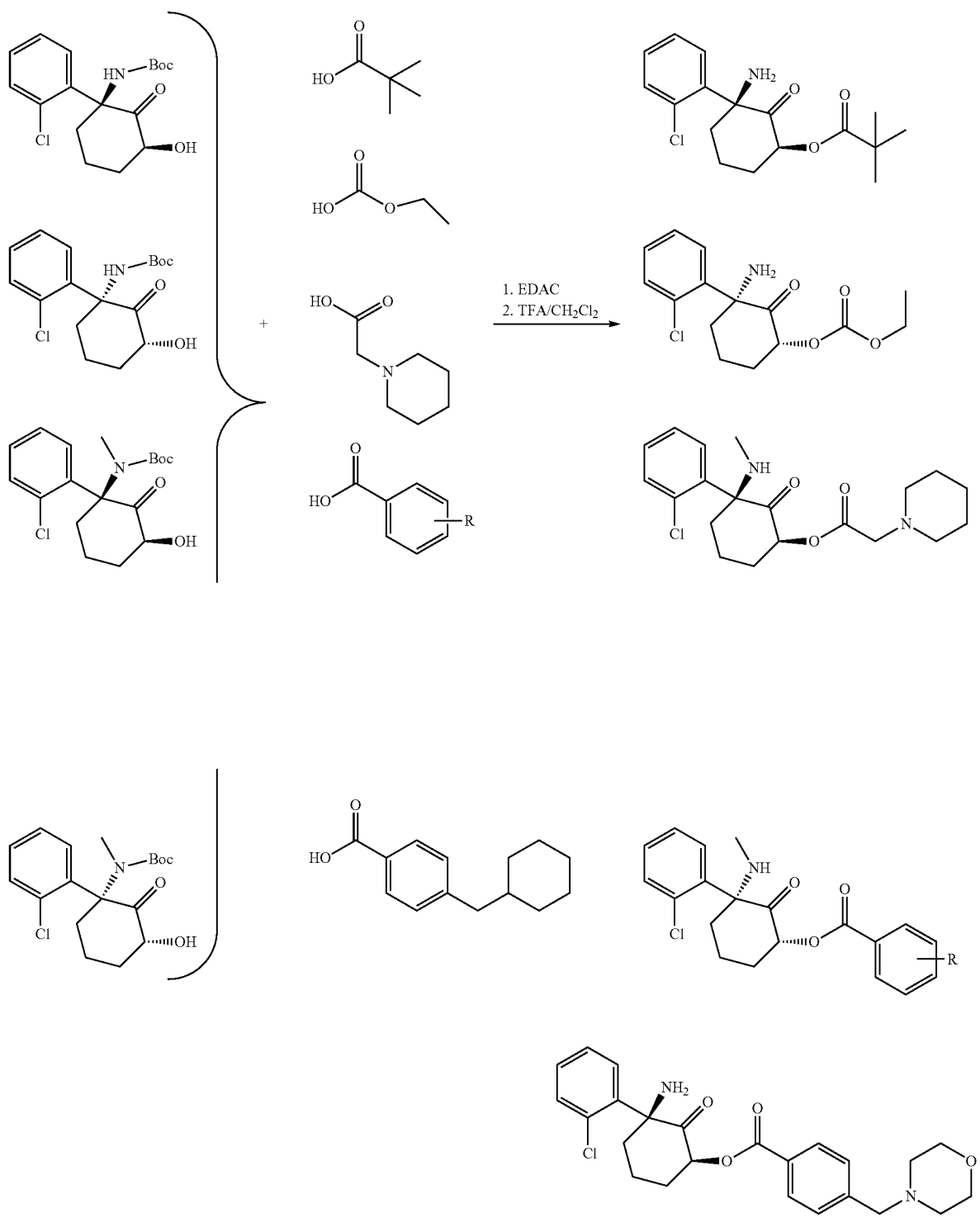
-continued
Methodology:   R Group
1. EDAC
2. TFA/CH$_2$Cl$_2$
R = Cl, F, H

Example 3

Synthesis of (+,−)-(2S,6R/2R,6S)-6-Hydroxynorketamine

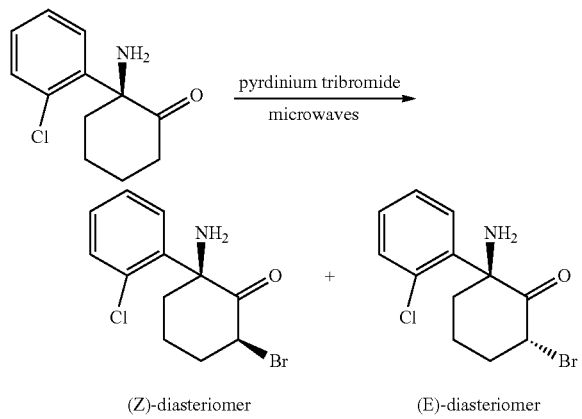

3:1 mixture of diasteriomers (separated by chromatography)

Synthesis of (+,−)-(Z+E)-6-Bromonorketamine. A sample of racemic (+,−)-norketamine (free base) (10.0 g, 35.8 mmol) in 50 mL glacial acetic acid was treated with pyridinium tribromide (16.4 g, 51.3 mmol). The resulting mixture was heated at 130° C. for 1 h using microwaves. The solvent was removed in vacuo and the crude material dissolved in CHCl₃ and washed with saturated NaHCO₃, dried (Na₂SO₄) and evaporated in vacuo leaving 12.4 g of a crude product mixture of diasteriomers (Z+E, 3:1). This was chromatographed using silica gel, eluting with a varying concentration of CH₂Cl₂/MeOH/Et₃N from (99.9/0/0.1) to (98.9/1/0.1) to give the pure separated isomers, (+,−)-(E)-6-bromonorketamine (1.22 g) (9% yield) and (+,−)-(Z)-6-bromonorketamine (6.6 g) (49% yield).

Analytical Data for (+,−)-(E)-6-bromonorketamine: ¹H NMR: (300 MHz, CDCl₃): δ 7.60 (m, 1H), 7.20-7.10 (m, 3H), 5.17 (dd, 1H, J=12.0 Hz, J=6.6 Hz), 2.72-2.39 (m, 3H), 2.36-2.08 (m, 1H), 1.96-1.82 (m, 2H), 1.69 (br s, 2H). MS: (ESI) m/z (relative intensity): 302 (77, M+H), 304 (100, M+H).

Analytical Data for (+,−)-(Z)-6-bromonorketamine: ¹H NMR: (300 MHz, CDCl₃): δ 7.62 (dd, 1H, J=1.8 Hz, J=7.5 Hz), 7.45-7.22 (m, 3H), 4.90 (dd, 1H, J=12.0 Hz, J=6.6 Hz), 2.70-2.63 (m, 1H), 2.58-2.41 (m, 2H), 2.24-2.09 (m, 2H), 2.10-1.78 (m, 3H). MS: (ESI) m/z (relative intensity): 302 (79, M+H), 304 (100, M+H). Gradient HPLC: Varian Pursuit C-18 (5 micron), 50×2 mm; 0.1% TFA in Water/0.1% TFA in Acetonitrile 95/5 to 5/95 over 5 min then hold; 0.200 mL/min; Total Ion Chromatogram (TIC); R$_t$ 7.03, product, 95% pure.

Synthesis of (+,−)-(2S,6R/2R,6S)-6-Hydroxynorketamine. A sample of racemic (+,−)-(Z)-6-bromonorketamine (2.71 g, 8.96 mmol) in absolute ethanol (20 mL) was treated with 1M ammonium formate (pH 6.8) (20 mL). The resulting solution was stirred under Ar for 10 days forming only a trace of product. The solvent was removed in vacuo and the crude product mixture dissolved in DMSO (10 mL) and purified by injections onto a preparative HPLC. Gradient HPLC: Waters Sunfire Prep C18 (10 micron), 150×30 mm; 5 mM Ammonium Formate in Water/Acetonitrile (90/10) for 5 min then (90/10) to (10/90) over 10 min then hold; 10 mL/min, 270 nm; R$_t$ 9.5 min. Product fractions were combined and evaporated in vacuo giving (+,−)-(2S,6R/2R,6S)-6-hydroxynorketamine (25 mg) (1% yield).

Analytical Data for (+,−)-(E)-6-Hydroxynorketamine: ¹H NMR: (300 MHz, CDCl₃): δ 7.62 (dd, 1H, J=1.8 Hz, J=7.5 Hz), 7.45-7.22 (m, 3H), 4.90 (dd, 1H, J=12.0 Hz, J=6.6 Hz), 2.70-2.63 (m, 1H), 2.58-2.41 (m, 2H), 2.24-2.09 (m, 2H), 2.10-1.78 (m, 3H). MS: (ESI) m/z (relative intensity): 240 (100, M+H). Gradient HPLC: Varian Pursuit C-18 (5 micron), 150×4.6 mm; 5 mM Ammonium Formate (pH 7.6)/Acetonitrile 80/20 for 5 min then 80/20 to 20/80 over 10 min then hold; 0.250 mL/min; Total Ion Chromatogram (TIC); R$_t$ 17.26, product, 95% pure.

Example 4

Additional Purified Hydroxynorketamine and Dehydroxynorketamine Forms (S)-5,6-dehydroxynorketamine

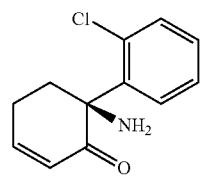 [SMILES: N[C@]1(c2ccccc2Cl)CCC=CC1=O]

¹H NMR: (400 MHz, CD₃OD): d 7.58 (dd, 1H, J=8.0 Hz, J=1.2 Hz), 7.49 (dt, 1H, J=7.6 Hz, J=1.6 Hz), 7.40 (dt, 1H, J=7.2 Hz, J=1.2 Hz), 7.33 (dd, 1H, J=8.0 Hz, J=1.6 Hz), 7.12-7.07 (m, 1H), 6.38-6.34 (m, 1H), 3.41-3.37 (m, 1H), 2.60-2.51 (m, 1H), 2.36-2.28 (m, 1H), 2.15-2.04 (m, 1H). MS: (ESI) m/z (relative intensity): 222 (100, M+H). Gradient HPLC: Varian Pursuit C-18 (3 micron), 50×2 mm, Acetonitrile/10 mM Ammonium Formate (pH 7) in Water: (2/98) for 2.5 min then (2/98) to (98/2) over 7.5 min then hold; 0.200 mL/min, 254 nm; R$_t$ 4.10 min; 95% pure. Chiral HPLC: Supelco Chiral AGP (5 micron), 100×4 mm; Acetonitrile/50 mM Ammonium Acetate in Water (pH 7.2) (10/90); 0.700 mL/min, 225 nm; R$_t$ 3.370 min; 98.48% pure.

(R)-5,6-dehydroxynorketamine hydrochloride

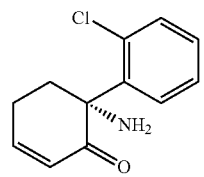 [SMILES: N[C@@]1(c2ccccc2Cl)CCC=CC1=O]

¹H NMR: (400 MHz, CD3OD): d 7.58 (dd, 1H, J=8.0 Hz, J=1.2 Hz), 7.49 (dt, 1H, J=7.6 Hz, J=1.6 Hz), 7.40 (dt, 1H, J=7.2 Hz, J=1.2 Hz), 7.33 (dd, 1H, J=8.0 Hz, J=1.6 Hz), 7.12-7.07 (m, 1H), 6.38-6.34 (m, 1H), 3.41-3.37 (m, 1H), 2.60-2.51 (m, 1H), 2.36-2.28 (m, 1H), 2.15-2.04 (m, 1H). MS: ESI) m/z (relative intensity): 222 (100, M+H). Gradient HPLC: Varian Pursuit C-18 (3 micron), 50×2 mm, Acetonitrile/10 mM Ammonium Formate (pH 7) in Water: (2/98) for 2.5 min then (2/98) to (98/2) over 7.5 min then hold; 0.200 mL/min, 254 nm; Rt 4.18 min; 95% pure. Chiral HPLC: Supelco Chiral AGP (5 micron), 100×4 mm; Acetonitrile/50 mM Ammonium Acetate in Water (pH 7.2) (10/90); 0.700 mL/min, 225 nm; Rt 8.059 min; 95.29% pure.

(2R,6R)-6-Hydroxynorketamine Hydrochloride

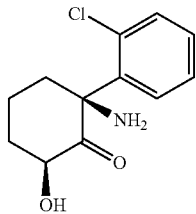 [SMILES: N[C@]1(c2ccccc2Cl)CCC[C@H](O)C1=O]

$^1$H NMR: (300 MHz, CD$_3$OD): δ 7.90-7.86 (m, 1H), 7.62-7.55 (m, 3H), 4.30 (dd, 1H, J=6.8 Hz, J=11.6 Hz), 3.26-3.18 (m, 1H), 2.33-2.27 (m, 1H), 2.00-1.60 (m, 4H). MS: (ESI) m/z (relative intensity): 240 (100, M+H). Gradient HPLC: Varian Pursuit C-18 (5 micron), 150×4.6 mm; 5 mM Ammonium Formate in Water/Acetonitrile (80/20) for 5 min then (80/20) to (20/80) over 10 min then hold; 0.250 mL/min, 270 nm; R$_t$ 13.05; 99% pure. Chiral HPLC: Supelco Chiral AGP (5 micron), 100×4 mm; 100% 50 mM Ammonium Acetate in Water (pH 7.2); 0.800 mL/min, 215 nm; R$_t$ 4.487 min; 97.68% pure.

(2S,6S)-6-Hydroxynorketamine Hydrochloride

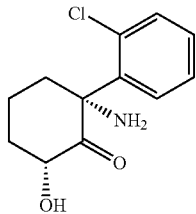 [SMILES: N[C@@]1(c2ccccc2Cl)CCC[C@@H](O)C1=O]

$^1$H NMR: (300 MHz, CD$_3$OD): d 7.90-7.86 (m, 1H), 7.62-7.55 (m, 3H), 4.30 (dd, 1H, J=6.8 Hz, J=11.6 Hz), 3.26-3.18 (m, 1H), 2.33-2.27 (m, 1H), 2.00-1.60 (m, 4H). MS: (ESI) m/z (relative intensity): 240 (100, M+H). Gradient HPLC: Varian Pursuit C-18 (5 micron), 150×4.6 mm; 5 mM Ammonium Formate in Water/Acetonitrile (80/20) for 5 min then (80/20) to (20/80) over 10 min then hold; 0.250 mL/min, 270 nm; R$_t$ 13.05; 99% pure. Chiral HPLC: Supelco Chiral AGP (5 micron), 100×4 mm; 100% 50 mM Ammonium Acetate in Water (pH 7.2); 0.800 mL/min, 215 nm; R$_t$ 5.574 min; 98.61% pure.

Example 5

Serine Racemase Inhibition Assay

Materials

D-serine (D-Ser), L-serine (L-Ser), D-alanine (D-Ala), L-alanine (L-Ala), D-arginine, (D-Arg), L-arginine (L-Arg), glycine (Gly), D-leucine (D-Leu), L-leucine (L-Leu), D-isoleucine (D-Iso), L-isoleucine (L-Iso), D-glutamic acid (D-Glu), L-glutamic acid (L-Glu), D-aspartic acid (D-Asp), L-aspartic acid (L-Asp), L-lysine (L-Lys), β-cyclodextrin (β-CD), 2-hydroxypropyl-β-cyclodextrin (HP-β-CD), methanol, acetonitrile (ACN), and fluorescein isothiocyanate (FITC) were obtained from Sigma-Aldrich (St. Louis, Mo., USA). De-ionized water was obtained from a Milli-Q system (Millipore, Billerica, Mass., USA). All other chemicals used were of analytical grade.

Cell Lines and Cell Culture

The cell lines selected for this study were PC-12 pheochromocytoma derived from rat adrenal medulla, human-derived 1321N1 astrocytoma, rat-derived C6 glioblastoma, and human-derived HepG2 hepatocellular carcinoma. All of the cell lines were obtained from ATCC (Manassas, Va., USA). The PC12 cells were maintained in RPMI7 1640 with L-Gln supplemented with 10% horse serum (heat inactivated), 5% FBS, 1% sodium pyruvate solution, 1% HEPES buffer and 1% penicillin/streptomycin solution. The 1321N1 and C6 cells were maintained in DMEM with L-Gln supplemented with 10% FBS and 1% penicillin/streptomycin solution. The HepG2 cells were maintained in E-MEM supplemented with 1% L-Gln, 10% FBS, 1% sodium pyruvate solution and 1% penicillin/streptomycin solution.

Dulbecco's Modified Eagle Medium (DMEM) with glutamine, Eagle's Minimum Essential Medium (E-MEM), RPMI-1640, trypsin solution, phosphate-buffered saline, fetal bovine serum (FBS), sodium pyruvate solution (100 mM), L-glutamine (L-Gln) (200 mM) and penicillin/streptomycin solution (containing 10,000 units/ml penicillin and 10,000 μg/ml streptomycin) were obtained from Quality Biological (Gaithersburg, Md., USA), horse serum (heat inactivated) was obtained from Biosource (Rockville, Md., USA) and HEPES (4-(2-hydroxyethyl)-1-piperazineethanesulfonic acid) buffer (1 M) was obtained from Mediatech Inc. (Manassas, Va., USA).

CE-LIF (Capillary Electrophoresis-Laser Induced Fluorescence) Analysis

Instrumentation: The CE separations were performed with a P/ACE MDQ system equipped with a laser-induced fluorescence detector (Beckman Instruments, Fullerton, Calif., USA). The laser-induced fluorescence detection was carried out with excitation at 488 nm and emission at 520 nm. An uncoated fused-silica capillary of 50 μm I.D. and effective length of 50 cm was used and the running buffer was composed of 0.5 mM HP-β-CD solution prepared in borate buffer [80 mM, pH 9.3]. The capillary was conditioned before each analysis by flushing successively with 0.1 N NaOH, 0.1 N H$_3$PO$_4$, H$_2$O and running buffer each for 4 min. Samples were injected with pressure at 0.5 p.s.i. for 1 s and separated using a voltage gradient in which separation voltage was 15 kV between 0-44 min, followed by 22 kV between 45-60 min. At 60 min, the voltage was reduced to 0 kV and the column washed for 4 min with 0.1 N NaOH followed by a 4 min wash with 0.1 N phosphoric acid. The total run time was 68 min. Quantification was accomplished using area ratios calculated for FITC-D-Ser with FITCD-Arg as the internal standard, where the concentration of the internal standard was set at 5 μM.

Standard solutions: A concentrated stock solution of 0.5 mM D-Ser in borate buffer [80 mM, pH 9.3] was used to prepare 0.25, 0.5, 1, 2, 4, 10, 20, 40, 80, and 100 μM solutions for the calibration curve. Standard solutions, 1 mM in borate buffer [80 mM, pH 9.3], of L-Ser, D-Ala, L-Ala, D-Arg, L-Arg, Gly, D-Leu, L-Leu, D-Iso, L-Iso, D-Glu, L-Glu, D-Asp, L-Asp, L-Lys were also prepared. A 100 μM solution of D-Arg in H$_2$O was used as the internal standard solution.

Sample preparation: Cells were collected and centrifuged for 5 min at 200×g at 4° C. The supernatant was discarded and the cells were suspended in 1.00 ml of $H_2O$, 0.050 ml of the internal standard was added and the resulting mixture vortex mixed for 1 min. A 4.00 ml aliquot of ACN was added and the suspension was sonicated for 20 min. The mixture was then centrifuged for 15 min at 2500×g at 4° C., the supernatant collected and stream dried under nitrogen. The residue was dissolved in 0.90 ml of borate buffer [80 mM, pH 9.3].

FITC labeling: FITC solution (3 mg/ml) was prepared in acetone and stored at −20° C. until use. For the derivatization of standard amino acids, a 0.05 ml aliquot of the internal standard solution was added to a 0.85 ml of the standard solution and 0.10 ml of FITC solution was added and the resulting solutions were placed in darkness for 12 h at room temperature. When cellular extracts were assayed, 0.10 ml of FITC solution was added to the 0.90 ml samples and the resulting solutions were placed in darkness for 12 h at room temperature.

Effect of Ketamine Metabolites on Serine Racemase Activity and Expression

Cells were seeded on 100×20 mm tissue culture plates and were maintained at 37° C. under humidified 5% $CO_2$ in air until they reached >70% confluence. The original media was replaced with media containing sequential concentrations of the test compounds and the plates were incubated for an additional 36 h. Compound concentrations of 0 to 100 nM were used, e.g. 10 nM, 20 nM, 50 nM, 75 nM and 100 nM.

The medium was removed, and the cells collected for analysis. All of the studies were done in triplicate.

Western Blotting

Cells were lysed with RIPA buffer containing ethylene glycol tetraacetic acid and ethylenediamine tetraacetic acid (Boston BioProducts, Ashland, Mass., USA). The lysis buffer contained a protease inhibitor cocktail composed of 4-(2-aminoethyl)benzenesulfonyl fluoride, pepstatin A, E-64, bestatin, leupeptin, and aprotinin (Sigma-Aldrich). Protein concentrations were determined using the bicinchoninic acid (BCA) reagent obtained from Pierce Biotechnology, Inc. (Rockford, Ill., USA). Proteins (20 μg/well) were separated on 4 to 12% precast gels (Invitrogen, Carlsbad, Calif., USA) using SDS-polyacrylamide gel electrophoresis under reducing conditions and then they were electrophoretically transferred onto polyvinylidene fluoride (PVDF) membrane (Invitrogen). Western blots were performed according to standard methods which involved blocking in 5% non-fat milk and incubated with the antibody of interest, followed by incubation with a secondary antibody conjugated with the enzyme horseradish peroxidase. The visualization of immunoreactive bands was performed using the ECL Plus Western Blotting Detection System (GE Healthcare, NJ, USA). The quantification of bands was done by volume densitometry using Image software and normalization to β-actin.

The primary antibodies for SR were obtained from Santa Cruz Biotechnology (Santa Cruz, Calif., USA), sc-48741, and Abcam (Cambridge, Mass., USA), ab45434, and the primary antibody for β-actin was obtained from Abcam, ab6276. The antibodies were used at a dilution recommended by the manufacturer.

Statistical Analysis

Graphpad Prism 4 (GraphPad Software, Inc., La Jolla, Calif., USA) running on a personal computer was used to perform all the statistical data analysis including EC50 and IC50 value calculations.

Certain compounds of Formula I discussed in this disclosure were tested in the above serine racemase assay, for NMDA receptor inhibition and inhibition of the nicotinic acetylcholine receptor subtype $α_7$. The assay for nicotinic acetylcholorine receptor subtype $α_7$ is given below in Example 6.

| Compounds | NMDAR $K_i$ (μM) | $IC_{50}$ ($α_7$) | $IC_{50}$ (D-Serine) |
|---|---|---|---|
| (S)-norKet | 2.25 ± 0.22 μM | Not Determined | 50-120 nM |
| (R)-norKet | 26.46 μM | Not available | 40-80 nM |
| (R,S)-norKet | Not Determined | At 100 nM the inhibition was 46% | Not Determined |
| (S)-DHNK | 38.95 μM | Not Determined | Not Determined |
| (R)-DHNK | 74.55 μM | Not Determined | Not Determined |
| (R,S)-DHNK | Not Determined | ~50 nM | 35-50 nM |
| (2S,6S)-HNK | 21.19 μM | At 100 nM the inhibition was 54% | 0.1-0.3 nM |
| (2R,6R)-HNK | >100 μM | At 100 nM the inhibition was 51% | 0.4-0.7 nM |

DHNK was found to be a potent inhibitor of the nACh receptor $α_7$ subtype while ketamine and norketamine are inactive at this receptor subtype.

Example 6

Effect of Compounds on Currents Evoked by Acetylcholine Receptors

Since nicotinic acetylcholine receptors (nAChR) have been validated as a target in analgesia we have investigated the activity of DHNK (dehydroxynorketamine) at two nAChR subtypes, $α_7$ and $α_3β_4$ nAChR. The patch clamp in a whole cell configuration was used to examine functional activity of ketamine, norketamine, and the DHNK and HNK metabolites on currents evoked by 280 micromolar acetylcholine in the KXα7R1. The data was obtained at −80 mV and normalized to the amplitude of current elicited by ACh alone, n=4.

| | | Mean | SE |
|---|---|---|---|
| (R,S)-norKet | 100 nM | 0.548 | 0.099 |
| | 1000 nM | 0.287 | 0.075 |
| (R,S)-DHNK | 100 nM | 0.407 | 0.053 |
| | 1000 nM | 0.205 | 0.013 |
| (2S,6S)-HNK | 100 nM | 0.461 | 0.06 |
| | 1000 nM | 0.361 | 0.07 |
| (2R,6R)-HNK | 100 nM | 0.489 | 0.077 |
| | 1000 nM | 0.354 | 0.084 |

What is claimed is:
1. A compound of the formula

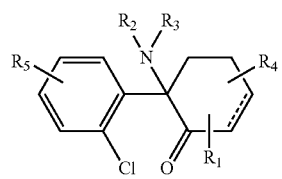

or a pharmaceutically acceptable salt thereof, wherein
$R_1$ is hydroxyl or -$A_1B_1$ where $A_1$ is —O—, —O(C=O)—, —(C=O)O—, —O(C=O)O—, —O(C=O)NR$_6$—, —OS(O)$_2$—, —OS(O)$_3$, or —OP(O)$_3$—, and $B_1$ is $C_1$-$C_8$alkyl, $C_2$-$C_8$alkenyl, $C_2$-$C_8$alkynyl, (carbocycle)$C_0$-$C_4$alkyl or (heterocycle)$C_0$-$C_4$alkyl, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy; with the proviso that -$A_1B_1$ is not (4-methylphenyl)-S(O)$_2$O—;

wherein the six-membered ring to which $R_1$ is bound is fully saturated when $R_1$ is hydroxyl or -$A_1B_1$;

$R_2$ is hydrogen or -$A_2B_2$ where $A_2$ is a bond, —O(C=O)—, —(C=O)O—, —S(O)$_2$—, —(S=O)NR$_6$—, or —(C=O)NR$_6$—, $B_2$ is $C_1$-$C_8$alkyl, $C_2$-$C_8$alkenyl, $C_2$-$C_8$alkynyl, $C_2$-$C_6$alkanoyl, (carbocycle)$C_0$-$C_4$alkyl, (heterocycle)$C_0$-$C_4$alkyl, or an amino acid or dipeptide covalently bound to $A_2$ by its C-terminus, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy; with the proviso that $B_2$ is not methyl when $A_2$ is a bond or —(C=O)O—;

$R_1$ is not hydroxyl when $R_2$ is hydrogen;

$R_3$ is hydrogen;

$R_4$ and $R_5$ are 0 or 1 or more substituents independently chosen from halogen, hydroxyl, amino, cyano, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy; and $R_6$ is hydrogen or $C_1$-$C_6$alkyl.

2. A compound or salt of claim 1, of the formula

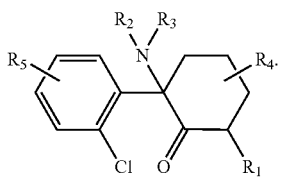

3. A compound of the formula

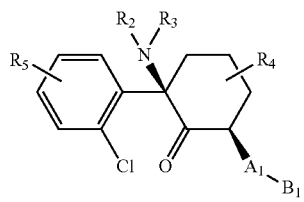

or a pharmaceutically acceptable salt thereof,
where $A_1$ is —O—, —O(C=O)—, or —O(C=O)O— and $B_1$ is $C_1$-$C_8$alkyl, $C_2$-$C_8$alkenyl, $C_2$-$C_8$alkynyl, (carbocycle)$C_0$-$C_4$alkyl or (heterocycle)$C_0$-$C_4$alkyl, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy;

$R_2$ is hydrogen or -$A_2B_2$ where $A_2$ is a bond, —O(C=O)—, —(C=O)O—, —S(O)$_2$—, —(S=O)NR$_6$—, or —(C=O)NR$_6$—, $B_2$ is $C_1$-$C_8$alkyl, $C_2$-$C_8$alkenyl, $C_2$-$C_8$alkynyl, $C_2$-$C_6$alkanoyl, (carbocycle)$C_0$-$C_4$alkyl, (heterocycle)$C_0$-$C_4$alkyl, or an amino acid or dipeptide covalently bound to $A_2$ by its C-terminus, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy; with the proviso that $B_2$ is not methyl when $A_2$ is a bond or —(C=O)O—;

$R_3$ is hydrogen or $C_1$-$C_6$alkyl;

$R_4$ and $R_5$ are 0 or 1 or more substituents independently chosen from halogen, hydroxyl, amino, cyano, $C_1$-$C_4$alkyl, $C_1$-$C_4$alkoxy, mono- and di-$C_1$-$C_4$alkylamino, $C_1$-$C_2$haloalkyl, and $C_1$-$C_2$haloalkoxy; and $R_6$ is hydrogen or $C_1$-$C_6$alkyl.

4. A compound or salt of claim 3, wherein
$R_3$ is hydrogen;
$R_4$ and $R_5$ are each 0 to 2 substituents independently chosen from halogen, hydroxyl, amino, $C_1$-$C_2$alkyl, and $C_1$-$C_2$alkyl; and
$R_6$ is hydrogen or methyl.

5. A compound or salt of claim 4, wherein
$R_2$ is -$A_2B_2$ where $A_2$ is a bond, —(C=O)O—, —S(O)$_2$—, —(S=O)NR$_6$—, or —(C=O)NR$_6$—, $B_2$ is $C_1$-$C_6$alkyl, $C_2$-$C_4$alkanoyl, (phenyl)$C_0$-$C_2$alkyl, ($C_3$-$C_7$cycloalkyl)$C_0$-$C_4$alkyl, (heterocycloalkyl)$C_0$-$C_2$alkyl, (5- or 6-membered heteroaryl)$C_0$-$C_2$alkyl, or an amino acid covalently bound to $A_2$ by its C-terminus, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, $C_1$-$C_2$haloalkyl, and $C_1$-$C_2$haloalkoxy.

6. A compound or salt of claim 4, where
$A_2$ is a bond or —(C=O)O— and $B_2$ is $C_2$-$C_6$alkyl, (phenyl)$C_0$-$C_2$alkyl, or ($C_3$-$C_7$alkyl)$C_0$-$C_4$alkyl, each of which is substituted with from 0 to 4 substituents independently chosen from halogen, hydroxyl, amino, cyano, $C_1$-$C_4$alkyl, $C_1$-$C_4$alkoxy, and mono- and di-($C_1$-$C_4$alkyl)amino.

7. A compound of the formula

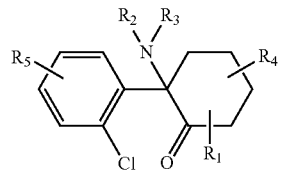

or a pharmaceutically acceptable salt thereof, wherein:
$R_1$ is -$A_1B_1$ where $A_1$ is —O—, —O(C=O)—, —(C=O)O—, —O(C=O)O—, —O(C=O)NR$_6$—, —OS(O)$_2$—, —OS(O)$_3$, or —OP(O)$_3$—, and $B_1$ is $C_1$-$C_8$alkyl, $C_2$-$C_8$alkenyl, $C_2$-$C_8$alkynyl, (carbocycle)$C_0$-$C_4$alkyl or (heterocycle)$C_0$-$C_4$alkyl, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy; with the proviso that -$A_1B_1$ is not (4-methylphenyl)-S(O)$_2$ O—;

$R_2$ is hydrogen;

$R_3$ is hydrogen;

$R_4$ and $R_5$ are each 0 to 2 substituents independently chosen from halogen, hydroxyl, amino, $C_1$-$C_2$alkyl, and $C_1$-$C_2$alkyl; and $R_6$ is hydrogen or methyl.

8. A compound or salt of claim 7, where $R_1$ is -$A_1B_1$ where $A_1$ is —O(C=O)— or —O(C=O) O—, and $B_1$ is $C_1$-$C_6$alkyl, (phenyl)$C_0$-$C_4$alkyl, ($C_3$-$C_7$cycloalkyl)$C_0$-$C_4$alkyl, (heterocycloalkyl)$C_0$-$C_2$alkyl, or (5- or 6-membered heteroaryl)$C_0$-$C_2$alkyl, each of which is substituted with from 0 to 4 substituents independently chosen from halogen, hydroxyl, amino, cyano, $C_1$-$C_4$alkyl, $C_1$-$C_4$alkoxy, $C_1$-$C_6$alkylester, mono- and di-($C_1$-$C_4$alkyl)amino, ($C_3$-$C_7$cycloalkyl)$C_0$-$C_2$alkyl, (heterocycloalkyl)$C_0$-$C_2$alkyl, $C_1$-$C_2$haloalkyl, and $C_1$-$C_2$haloalkoxy.

9. A method of treating bipolar depression, major depressive disorder, schizophrenia, Alzheimer's dementia, amyotrophic lateral sclerosis, complex regional pain syndrome (CRPS), chronic pain, or neuropathic pain comprising administering an effective amount of a compound or salt of claim 1, to a patient in need of such treatment.

10. The method of claim 9, wherein an effective amount is an amount effective to decrease painful symptoms; wherein a decrease in painful symptom is the achievement of a 50% or greater reduction of painful symptoms on a pain rating scale.

11. A pharmaceutical composition comprising a compound or salt of claim 1, together with a pharmaceutically acceptable carrier.

12. The pharmaceutical composition of claim 11, wherein the composition is a solution and contains from about 0.05 mg/ml to about 0.5 mg/ml.

13. A compound or salt of claim 8, of the formula

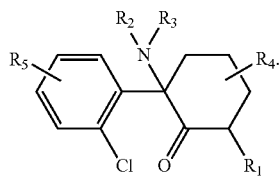

14. The pharmaceutical composition of claim 11, wherein the composition is formulated for oral administration, intravenous administration, or intramuscular injection.

15. A method of treating bipolar depression, major depressive disorder, schizophrenia, Alzheimer's dementia, amyotrophic lateral sclerosis, complex regional pain syndrome (CRPS), chronic pain, or neuropathic pain comprising administering an effective amount of a compound or salt of claim 3, to a patient in need of such treatment.

16. A pharmaceutical composition comprising a compound or salt of claim 3, together with a pharmaceutically acceptable carrier.

17. The pharmaceutical composition of claim 3, wherein the composition is formulated for oral administration, intravenous administration, or intramuscular injection.

18. The pharmaceutical composition of claim 3, wherein the composition is a solution and contains from about 0.05 mg/ml to about 0.5 mg/ml.

19. A method of treating bipolar depression, major depressive disorder, schizophrenia, Alzheimer's dementia, amyotrophic lateral sclerosis, complex regional pain syndrome (CRPS), chronic pain, or neuropathic pain comprising administering an effective amount of a compound or salt of claim 7, to a patient in need of such treatment.

20. A pharmaceutical composition comprising a compound or salt of claim 7, together with a pharmaceutically acceptable excipient.

21. The pharmaceutical composition of claim 7, wherein the composition is formulated for oral administration, intravenous administration, or intramuscular injection.

22. The pharmaceutical composition of claim 7, wherein the composition is a solution and contains from about 0.05 mg/ml to about 0.5 mg/ml.

* * * * *